(12) United States Patent
Kume et al.

(10) Patent No.: US 10,371,680 B2
(45) Date of Patent: Aug. 6, 2019

(54) SENSOR

(71) Applicant: NGK Spark Plug Co., LTD., Nagoya (JP)

(72) Inventors: Makoto Kume, Inuyama (JP); Shingo Ito, Ichinomiya (JP); Takehiro Oba, Kounan (JP); Shinya Miyamoto, Kounan (JP); Suguru Kyoumoto, Iwakura (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 276 days.

(21) Appl. No.: 15/414,808

(22) Filed: Jan. 25, 2017

(65) Prior Publication Data

US 2017/0212090 A1    Jul. 27, 2017

(30) Foreign Application Priority Data

Jan. 25, 2016 (JP) ................................. 2016-011639
Jan. 23, 2017 (JP) ................................. 2017-009583

(51) Int. Cl.
*G01N 33/00* (2006.01)
*G01N 27/407* (2006.01)

(52) U.S. Cl.
CPC ....... *G01N 33/0036* (2013.01); *G01N 27/407* (2013.01); *G01N 27/4077* (2013.01); *G01N 33/0009* (2013.01)

(58) Field of Classification Search
CPC ............... G01N 33/0036–006; G01N 27/4077
See application file for complete search history.

(56) References Cited

U.S. PATENT DOCUMENTS

2008/0223110 A1*  9/2008  Weyl .................. G01N 27/4077
                                                          73/31.05

FOREIGN PATENT DOCUMENTS

DE        19924319 C2 *  5/2001  ......... G01N 27/4077
JP        2003-185620 A    7/2003

* cited by examiner

*Primary Examiner* — Paul M. West
(74) *Attorney, Agent, or Firm* — Leason Ellis LLP

(57) ABSTRACT

A gas sensor is provided with a metal shell protecting member formed of a material superior in heat resistance to a metal shell, whereby a high-temperature measurement target (exhaust gas) is prevented from being in direct contact with a region, of a protector internal region of the metal shell, on the front side relative to a protector opposing surface. That is, in the gas sensor, it is possible to suppress corrosion, due to high temperature, of a region, of the protector internal region of the metal shell, on the front side relative to the protector opposing surface (an inner surface and a front end surface of a protector fixing portion), while the metal shell is formed of a material (SUS430) that can be subjected to working (crimping or the like) accompanied with deformation. Therefore, heat resistance of the entire sensor can be improved.

11 Claims, 12 Drawing Sheets

SENSOR

This application claims the benefit of Japanese Patent Applications No. 2016-011639, filed Jan. 25, 2016 and 2017-009583, filed Jan. 23, 2017, all of which are incorporated herein in their entireties by reference.

FIELD OF THE INVENTION

The present invention relates to a sensor including: a sensor element having a detection portion; a metal shell that holds the sensor element via an element holding member; and an element protector that is formed in a shape covering the sensor element and is fixed to the metal shell.

BACKGROUND OF THE INVENTION

A sensor for detecting state quantities (gas concentration, temperature, etc.) of a measurement target has been known. For example, a sensor includes: a sensor element having a detection portion; a metal shell that holds the sensor element via an element holding member; and an element protector that is formed in a shape covering the sensor element and is fixed to the metal shell (Japanese Patent Application Laid-Open (kokai) No. 2003-185620).

As an example of such a sensor, a gas sensor for detecting a specific gas contained in a measurement target gas has been known. A gas sensor is used for, for example, detecting a specific gas (oxygen, NOx, or the like) contained in an exhaust gas from an internal combustion engine.

Regarding a sensor applied to use in which the temperature of a measurement target is high, improvement of heat resistance can be achieved by, for example, forming an element protector, which is a member directly contacting the measurement target, of a material having excellent heat resistance.

Problems to be Solved by the Invention

However, even if the heat resistance of the element protector, which is a member of the sensor, is improved, a risk of corrosion of the metal shell due to the high-temperature measurement target still remains.

That is, since an end portion, of opposed end portions of the metal shell, on which the detection portion of the sensor element is disposed, is in direct contact with the measurement target, this end portion may be subjected to corrosion due to the high-temperature measurement target. To this end portion of the metal shell, the element protector for protecting the sensor element is fixed. Therefore, if the strength of the metal shell is reduced due to corrosion that occurs at the end portion of the metal shell, the element protector may fall off.

The metal shell may have a structure in which another member is fixed thereto by working accompanied with deformation, such as crimping. If the metal shell having the above structure is formed of a material having excellent heat resistance to improve the heat resistance thereof, it is difficult to perform the working accompanied with deformation on the metal shell.

Therefore, an object of the present invention is to provide a sensor capable of improving heat resistance thereof while including a metal shell formed of a material that can be subjected to the working accompanied with deformation.

SUMMARY OF THE INVENTION

Means for Solving the Problems

A gas sensor according to an aspect of the present invention includes a sensor element, a metal shell, an element protector, and a metal shell protecting member.

The sensor element is formed in an elongated shape extending in the axial direction, and includes a detection portion at the front side thereof.

The metal shell is formed in a tubular shape having a through-hole extending from a front-side opening thereof to a rear-side opening thereof. The metal shell holds, via an element holding member, the sensor element disposed in the through-hole. At this time, the sensor element is disposed in the through-hole, with the detection portion projecting from the front-side opening of the metal shell.

The element protector includes an opening, through which a measurement target passes, and is formed in a tubular shape. The element protector is fixed to the front side of the metal shell.

The metal shell includes, at an outer surface thereof, a protector opposing surface that opposes a rear end portion of the element protector.

The sensor includes a metal shell protecting member. The metal shell protecting member, together with the element protector, is configured to cover a predetermined region of the metal shell.

The predetermined region covered with the protector and the metal shell protecting member includes: at least a part of a front end surface of the metal shell; at least a part of an inner surface of the through-hole; and at least a part of a radial outer surface of the metal shell, which is connected with the front end surface of the metal shell.

Since the above sensor includes the metal shell protecting member and the element protector, a high-temperature measurement target is prevented from being in direct contact with the predetermined region of the metal shell (at least a part of the front end surface of the metal shell, at least a part of the inner surface of the through-hole, and at least a part of the radial outer surface connecting with the front end surface of the metal shell). Thus, in this sensor, corrosion of the predetermined region of the metal shell due to high temperature can be suppressed while the metal shell is formed of a material that can be subjected to working (crimping or the like) accompanied with deformation, whereby the heat resistance of the entire sensor can be improved.

The above sensor realizes protection of the metal shell by being provided with the minimum required metal shell protecting member while utilizing the element protector required for protecting the sensor element. Therefore, the heat resistance of the entire sensor can be improved while suppressing considerable increase in production cost.

Therefore, according to the above sensor, the heat resistance can be improved while including the metal shell formed of a material that can be subjected to working accompanied with deformation.

In the above sensor, when a protector internal region is defined to include: a region of an inner surface of the through-hole of the metal shell, which is provided on the front side relative to the element holding member; a region of the radial outer surface of the metal shell, which is covered with the element protector; and the front end surface of the metal shell, the metal shell protecting member and the element protector may cover at least a region of the protector internal region of the metal shell, which is provided on the front side relative to the protector opposing surface.

Since, in the above sensor, the metal shell protecting member and the element protector cover at least a region, of the protector internal region of the metal shell, on the front side relative to the protector opposing surface, a high temperature measurement target is prevented from being in direct contact with a region, of the protector internal region of the metal shell, on the front side relative to the protector opposing surface. Thus, in this sensor, corrosion of the protector internal region of the metal shell due to high temperature can be suppressed while the metal shell is formed of a material that can be subjected to working (crimping or the like) accompanied with deformation, whereby the heat resistance of the entire sensor can be improved.

In particular, a portion, of the metal shell, on the front side relative to the protector opposing surface has a restriction regarding increase in its dimension in the radial direction of the sensor. Therefore, it is difficult to ensure a large "thickness" from the inner surface of the through-hole to an outer surface of this portion.

Accordingly, this portion is likely to be reduced in strength and broken when corrosion or the like occurs due to influence of high temperature. In contrast, by adopting the structure in which the metal shell protecting member and the element protector cover at least a region, of the protector internal region of the metal shell, on the front side relative to the protector opposing surface, corrosion due to influence of high temperature can be suppressed, thereby suppressing breakage of the metal shell.

In the above sensor, the metal shell protecting member may be formed in a tubular shape having an insertion hole through which the sensor element is inserted.

The metal shell protecting member having such a shape can be disposed in the through-hole of the metal shell, with the sensor element being inserted through the insertion hole, and can cover at least a region, of the protector internal region, on the front side relative to the protector opposing surface.

The tubular shape may be a multistage tubular shape in which tubular parts having different radial dimensions are connected to each other via a step portion, or may be a flanged tubular shape having a tubular part, and a flange part projecting radially outward with respect to the tubular part.

In the above sensor, the metal shell protecting member may include a protector contact portion that is in contact with an inner surface of the element protector over a circumferential direction.

By providing the protector contact portion, formation of a gap between the metal shell protecting member and the element protector can be suppressed, and thus the measurement target (gas or the like) is suppressed from reaching the metal shell through the outer side of the metal shell protecting member.

As described above, since the metal shell protecting member is provided with the protector contact portion, the measurement target is not likely to be in direct contact with the metal shell, thereby further suppressing corrosion of the metal shell due to high temperature, and breakage of the metal shell.

In the above sensor, an inward projecting portion that projects inward may be provided at a rear side of the metal shell protecting member.

By providing the inward projecting portion, the measurement target that moves in the metal shell protecting member toward the rear end of the metal shell protecting member collides against the inward projecting portion, whereby the moving direction of the measurement target can be changed. Thus, the measurement target is suppressed from reaching the metal shell through the inner side of the metal shell protecting member.

Since the metal shell protecting member has the inward projecting portion, the measurement target is not likely to be in direct contact with the metal shell, thereby further suppressing corrosion of the metal shell due to high temperature, and breakage of the metal shell.

In the above sensor, the metal shell protecting member may be formed of a material superior in heat resistance to the metal shell.

Thus, even when the sensor is applied to use in which the temperature of the measurement target exceeds the heat resistant temperature of the metal shell, since the predetermined region of the metal shell can be protected by the metal shell protecting member, corrosion of the predetermined region of the metal shell due to high temperature can be suppressed. Thus, the heat resistance of the entire sensor can be improved.

The "material superior in heat resistance to the metal shell" means a material that is less likely to be corroded due to high temperature than the material of the metal shell.

In the above sensor, the metal shell protecting member may be formed of a metal material.

The metal shell protecting member may be formed by using a ceramic material or the like. However, when using a metal material, the thickness of the metal shell protecting member can be reduced while achieving the same strength, as compared to the case of using a ceramic material or the like.

Thus, a large space can be ensured between the metal shell protecting member and the sensor element, whereby thermal influence on the sensor element by the temperature (amount of heat) of the metal shell protecting member can be suppressed.

In the above sensor, the metal shell protecting member may be formed of a material having corrosion resistance higher than that of the metal shell.

By providing the metal shell protecting member, corrosion of the metal shell protecting member due to the measurement target can be suppressed, and corrosion of the metal shell due to the measurement target can be suppressed.

Even when the metal shell is formed, not of a noble metal material such as Pt having high catalytic ability, but of a metal material such as stainless steel having low catalytic ability, if high-temperature oxidation or corrosion progresses, the metal shell may have high catalytic ability under such high-temperature environment (e.g., 600° C. or more). In particular, if iron, which is used as a base material of stainless steel, is oxidized, the catalytic ability thereof under high temperature is enhanced, and iron may have ability to burn inflammable gas such as HC or ammonia. Therefore, when the metal shell is formed by using a metal material that is inferior in corrosion resistance such as high-temperature oxidation resistance or acid resistance, the inner wall surface of the through-hole of the metal shell may fall off after being corroded. If chips of the metal shell, which have fallen off due to shock, water, moisture, or the like, attach to the surface of the electrode of the sensor element, the detection result of the inflammable gas may be adversely affected.

Therefore, in the above sensor, the metal shell protecting member may cover a region, of the inner surface of the through-hole, on the front side relative to the element holding member, and may be in contact with the element holding member.

By providing the metal shell protecting member having the above structure, the inner surface of the through-hole is prevented from being in direct contact with the measurement target, whereby corrosion of the metal shell due to the measurement target can be suppressed. Thus, falling of a part of the metal shell due to corrosion can be suppressed, and attachment of chips of the metal shell, which have fallen off, to the sensor element can be suppressed, thereby suppressing occurrence of an error in a sensor output due to the chips.

In the above sensor, the element holding member may include: a ceramic holder that is in contact with the sensor element; and a metal holder that is disposed outward relative to the ceramic holder and is in contact with the metal shell. The metal shell protecting member may cover a region, of the inner surface of the through-hole, on the front side relative to the element holding member, and may be in contact with at least one of the ceramic holder and the metal holder.

By providing the element holding member and the metal shell protecting member having the above structures, the inner surface of the through-hole is prevented from being in direct contact with the measurement target, whereby corrosion of the metal shell due to the measurement target can be suppressed. Thus, attachment of chips of the metal shell, which have fallen off due to corrosion, to the sensor element can be suppressed, thereby suppressing occurrence of an error in a sensor output due to the chips.

Effects of the Invention

According to the sensor of the present invention, it is possible to improve the heat resistance while including the metal shell formed of a material that can be subjected to working accompanied with deformation.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

Hereinafter, embodiments to which the present invention is applied will be described with reference to the drawings.

The present invention is not limited to the embodiments described below and may be implemented in various alternative embodiments as far as they fall within the technical scope of the present invention.

1. First Embodiment 1-1. Overall Structure

As an example of a first embodiment, an oxygen sensor (hereinafter also referred to as "gas sensor 1") will be described, which is mounted to an exhaust pipe of an internal combustion engine so that a front end portion thereof is projected into the exhaust pipe, and which detects oxygen in an exhaust gas. The gas sensor 1 is mounted to, for example, an exhaust pipe of a vehicle such as an automobile or a motorcycle.

First, the structure of the gas sensor 1 according to the present embodiment will be described with reference to FIG. 1.

Figure 1:
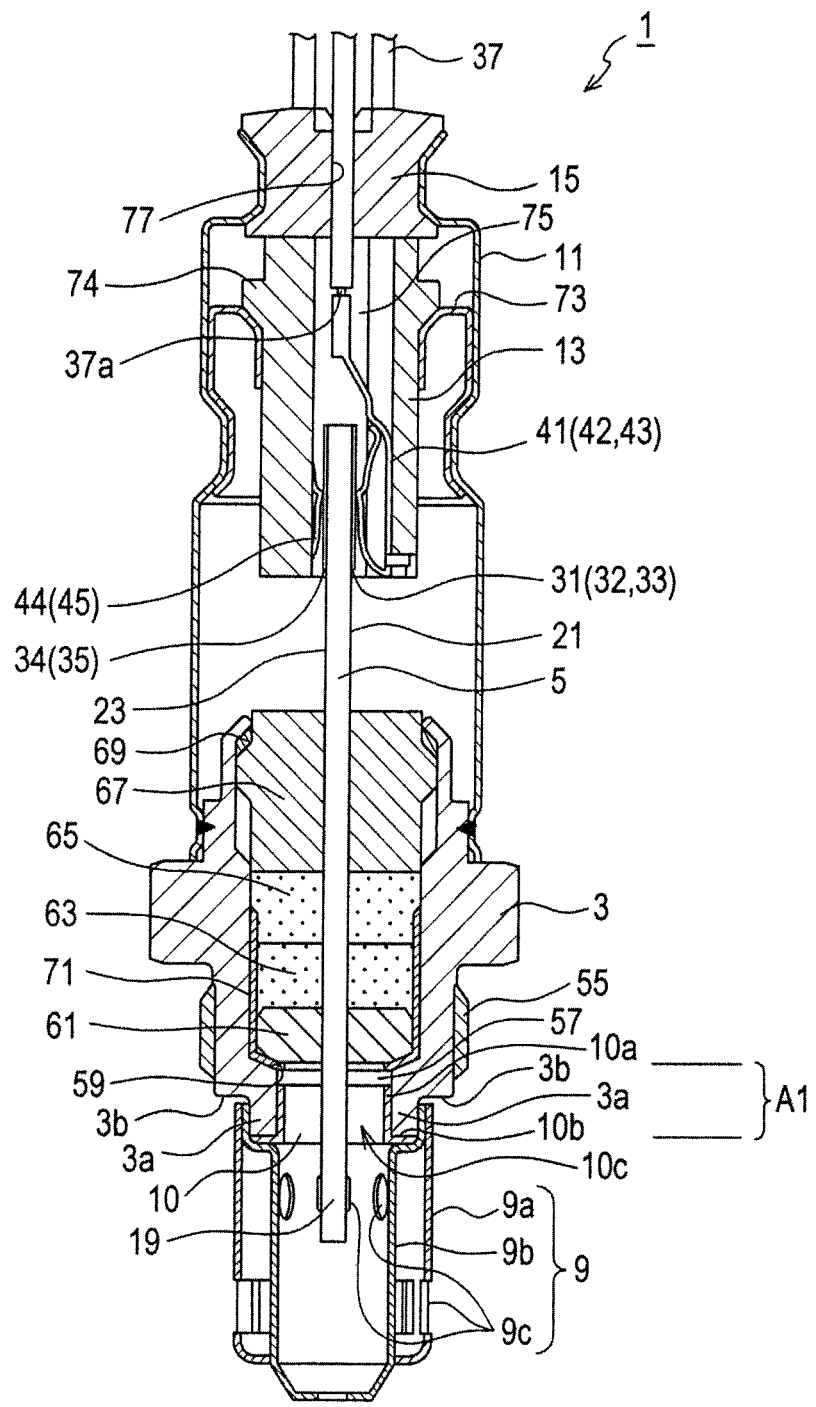
FIG. 1 is a cross-sectional view showing an overall structure of a gas sensor.

In FIG. 1, the downward direction is a direction toward a front end of the gas sensor, and the upward direction is a direction toward a rear end of the gas sensor.

The gas sensor 1 includes: a tubular metal shell 3 fixed to an exhaust pipe (not shown); a plate-shaped detection element 5 that is inserted through the metal shell 3 and extends in an axial direction (longitudinal direction of the gas sensor 1: up-down direction in FIG. 1); an element protector 9 that is disposed on the front side (lower side in FIG. 1) of the metal shell 3 and covers a front end portion of the detection element 5; a metal shell protecting member 10 disposed at a front end of the metal shell 3; an outer casing 11 that is mounted to the rear side (upper side in FIG. 1) of the metal shell 3 and covers an outer periphery of the detection element 5; a separator 13 (ceramic separator 13) that is disposed inside the outer casing 11 and houses a rear end portion of the detection element 5; and a closing member 15 that closes the rear side of the outer casing 11.

The detection element 5 is configured as follows. That is, a detection portion 19 covered with a protection layer is formed on the front side to be directed to a measurement target (exhaust gas or the like), and electrode terminal portions (first to fifth electrode terminal portions) 31, 32, 33, 34, and 35 are formed on a first plate surface 21 and a second plate surface 23 that are front and rear surfaces among outer surfaces of the detection element 5 on the rear side.

The detection element 5 is fixed inside the metal shell 3, with the detection portion 19 on the front side projecting from the front end of the metal shell 3 fixed to the exhaust pipe, and the electrode terminal portions 31 to 35 on the rear side projecting from the rear end of the metal shell 3.

To the electrode terminal portions 31 to 35, connection terminals (first to fifth connection terminals) 41, 42, 43, 44, and 45 as metal terminals are connected, respectively. That is, in the ceramic separator 13, the connection terminals 41 to 45 are disposed between the detection element 5 and the ceramic separator 13, and therefore are electrically connected to the electrode terminal portions 31 to 35 of the detection element 5, respectively. The connection terminals 41 to 45 are formed of a heat-resistant metal having elasticity (e.g., stainless steel or the like).

The connection terminals 41 to 45 are electrically connected to (five) lead wires 37 (specifically, metallic core wires 37a in the lead wires 37) inserted into the sensor from the outside, thereby forming current paths for currents that flow between external equipment to which the lead wires 37 are connected, and the electrode terminal portions 31 to 35 (in FIG. 1, only three lead wires 37 are shown).

Figure 2:
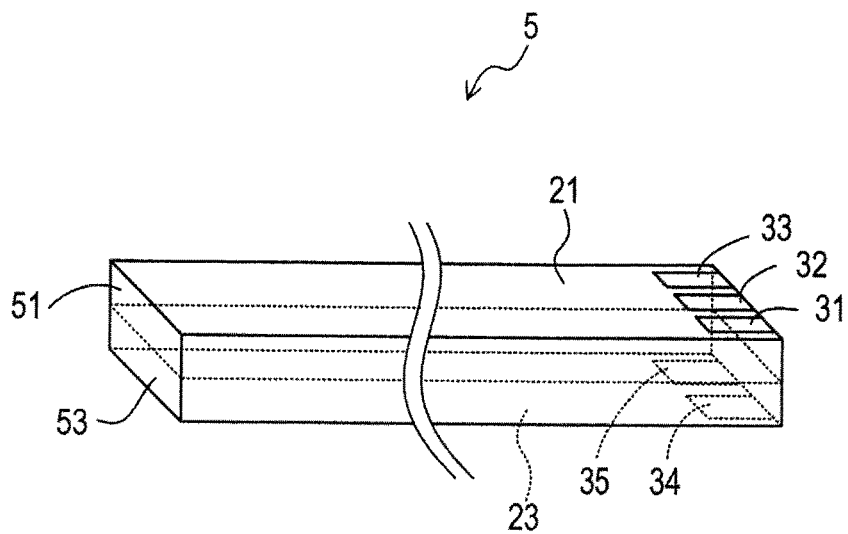
FIG. 2 is a perspective view showing a schematic structure of a detection element used for the gas sensor.

FIG. 2 is a perspective view showing a schematic structure of the detection element 5.

As shown in FIG. 2, the detection element 5 has a rectangular parallelepiped shape, in which a plate-shaped element portion 51 extending in the axial direction (right-left direction in FIG. 2) and a plate-shaped heater 53 extending in the axial direction are stacked, and has a rectangular cross section perpendicular to the axial direction.

Since the detection element 5 used for the gas sensor 1 is a conventionally known detection element, detailed description of the internal structure and the like of the detection element 5 will be omitted.

Referring back to FIG. 1, the metal shell 3 is a tubular member having, at an outer surface thereof, a screw portion 55 for fixing the metal shell 3 to the exhaust pipe, and having a through-hole 57 at an axial center thereof. In the through-hole 57, a shelf portion 59 projecting radially inward is formed. The metal shell 3 is formed of a metal material (e.g., stainless steel).

In the through-hole 57 of the metal shell 3, an annular holder 61 (ceramic holder 61) formed by using an insulating material (e.g., alumina or the like), annular powder-charged layers 63 and 65 (talc rings 63 and 65), and an annular sleeve 67 (ceramic sleeve 67) formed by using an insulating material (e.g., alumina or the like) are disposed in order from the front side to the rear side so as to surround the periphery of the detection element 5 in the radial direction.

A crimping packing 69 is disposed between the ceramic sleeve 67 and a rear end portion of the metal shell 3. A tubular metal holder 71 for holding the talc ring 63 and the ceramic holder 61 is disposed between the ceramic holder 61 and the shelf portion 59 of the metal shell 3. The rear end portion of the metal shell 3 is crimped via the crimping packing 69 so as to press the ceramic sleeve 67 toward the front side.

The element protector 9 is a tubular member mounted to a front-side outer circumference of the metal shell 3 by welding or the like (not shown) so as to cover the projecting portion of the detection element 5. The element protector 9 is formed by using a heat-resistant material (e.g., NCF601 or the like). The element protector 9 has a double structure including an outer protector 9a and an inner protector 9b. A plurality of holes 9c, which allow gas to pass therethrough, are formed at, for example, a side wall of the element protector 9.

The ceramic separator 13 is a tubular member formed by using an insulating material (e.g., alumina or the like), and is held in the outer casing 11 at the rear side by a tubular metal holder 73 disposed in the outer casing 11 at the rear side. The ceramic separator 13 has an annular flange portion 74 projecting outward from the outer surface thereof. By the flange portion 74 being supported by the metal holder 73, the ceramic separator 13 is held in the outer casing 11.

In the ceramic separator 13, a through-hole 75 is formed in the axial direction. The rear end portion (the electrode terminal portions 31 to 35) of the detection element 5 as well as the connection terminals 41 to 45 electrically connected to the electrode terminal portions 31 to 35 are stored in the through-hole 75.

The closing member 15 is a grommet formed by using a flexible material (e.g., fluororesin). The closing member 15 is disposed in the outer casing 11 at the rear side so as to be in contact with the rear end of the ceramic separator 13. The closing member 15 is fixed to the outer casing 11 by the outer casing 11 being crimped inward from the outside.

The lead wires 37 are connected (by crimping) to rear ends of the connection terminals 41 to 45 and are inserted through a through-hole 77 that is formed penetrating the closing member 15, thereby to be extended to the outside.

1-2. Metal Shell Protecting Member

Next, the metal shell protecting member 10 as a main part of the present embodiment will be described.

Figure 3:
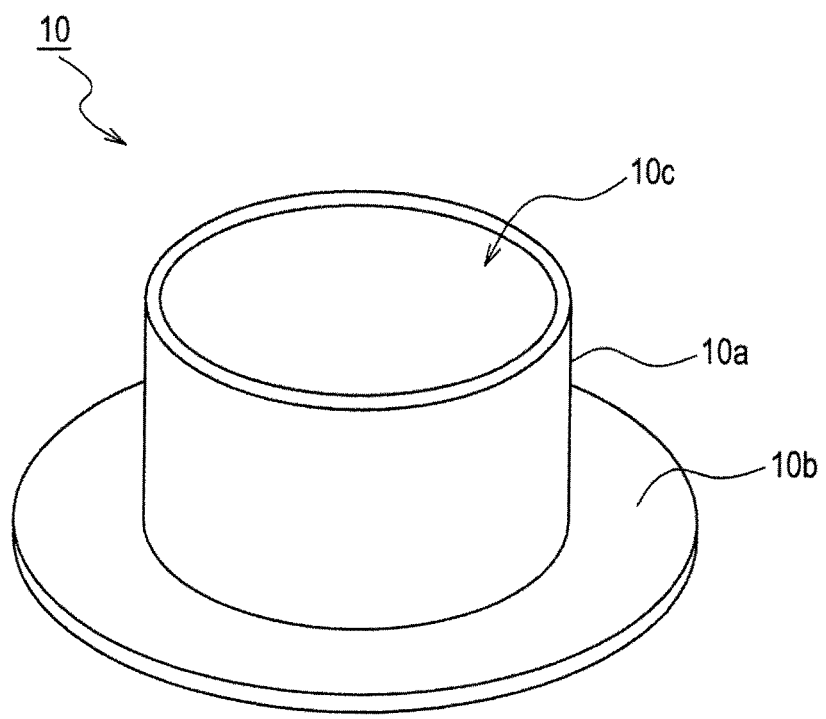
FIG. 3 is a perspective view showing an external appearance of a metal shell protecting member.

FIG. 3 is a perspective view showing an external appearance of the metal shell protecting member 10.

The metal shell protecting member 10 includes a tubular portion 10a and a flange portion 10b. In the tubular portion 10a, an insertion hole 10c is formed, which penetrates in the axial direction and through which the detection element 5 is to be inserted. The metal shell protecting member 10 is formed of a heat-resistant metal material (NCF601 or SUS310).

The tubular portion 10a is formed in a cylindrical shape in which an outer diameter thereof perpendicular to the axial direction is equal to an inner diameter of the through-hole 57 of the metal shell 3.

The flange portion 10b is formed at a front end portion of the tubular portion 10a so as to project outward in the circumferential direction.

As shown in FIG. 1, the metal shell protecting member 10 is disposed at the front end portion of the metal shell 3 such that the tubular portion 10a is in contact with a front-side inner surface of the through-hole 57 of the metal shell 3, and the flange portion 10b is in contact with a front end surface of the metal shell 3. In addition, the flange portion 10b of the metal shell protecting member 10 is in contact with an inner surface of the element protector 9 (specifically, the inner protector 9b) entirely in the circumferential direction.

The metal shell 3 is formed of stainless steel. In the present embodiment, the metal shell 3 is formed of SUS430. The SUS430 is a material that can be subjected to working accompanied with deformation (crimping or the like). The metal shell 3 formed of the above material is subjected to crimping at the rear end portion thereof, thereby to press the ceramic sleeve 67 toward the front side through the crimping packing 69.

The metal shell 3 includes a protector fixing portion 3a for fixing the element protector 9 to the front end thereof. The protector fixing portion 3a is formed so as to have a thickness (a dimension from an inner surface thereof facing the through-hole 57 to an outer surface thereof being in contact with the element protector 9) smaller than the thickness of the screw portion 55 of the metal shell 3.

The metal shell 3 includes a protector opposing surface 3b at an outer surface thereof. The protector opposing surface 3b is formed so as to oppose the rear end portion of the element protector 9 fixed to the protector fixing portion 3a. The protector opposing surface 3b of the present embodiment is formed as a plane perpendicular to the axial direction (in other words, a plane opposing the front side) at a portion, of the outer surface of the metal shell 3, on the front side relative to the screw portion 55.

That is, the protector fixing portion 3a is formed so as to have an outer diameter smaller than that of the screw portion 55 of the metal shell 3, and as a result, the protector opposing surface 3b is formed on the front side relative to the screw portion 55.

A protector internal region A1 is defined to include: a region, of the inner surface of the through-hole 57 of the metal shell 3, on the front side relative to the ceramic holder 61 (element holding member 61); a region, covered with the element protector 9, of the outer surface of the metal shell 3 (specifically, of the outer surface, a radially outward surface connecting with the front end surface of the metal shell 3); and the front end surface of the metal shell 3. In the present embodiment, the protector internal region A1 is a region composed of: a region, of the inner surface of the through-hole 57, on the front side relative to the ceramic holder 61; a portion, in contact with the element protector 9, of the radially outer surface of the metal shell 3; and a front end surface of the protector fixing portion 3a.

The metal shell protecting member 10 is disposed so as to cover at least a region, of the protector internal region A1 of the metal shell 3, on the front side relative to the protector opposing surface 3b (in other words, a region corresponding to the inner surface and the front end surface of the protector fixing portion 3a). Specifically, the tubular portion 10a of the metal shell protecting member 10 covers a region, of the inner surface of the through-hole 57, on the front side relative to the protector opposing surface 3b, while the flange portion 10b of the metal shell protecting member 10 covers the front end surface of the protector fixing portion 3a. Therefore, at least a region, of the protector internal region A1, on the front side relative to the protector opposing surface 3b is covered with the metal shell protecting member 10 and the element protector 9.

The heat-resistant metal material (NCF601 or SUS310) forming the metal shell protecting member 10 is superior in heat resistance to the material (SUS430) forming the metal shell 3. In addition, the heat-resistant metal material (NCF601 or SUS310) forming the metal shell protecting member 10 is superior in corrosion resistance to the material (SUS430) forming the metal shell 3.

1-3. Effects

As described above, the gas sensor 1 according to the present embodiment is provided with the metal shell protecting member 10 that is formed of a material superior in heat resistance to the metal shell 3, whereby a high-temperature measurement target (exhaust gas) is prevented from being in direct contact with a region, of the protector internal region A1 of the metal shell 3, on the front side relative to the protector opposing surface 3b.

That is, in the gas sensor 1, it is possible to suppress corrosion due to high temperature, of a region, of the protector internal region A1 of the metal shell 3, on the front side relative to the protector opposing surface 3b (i.e., the inner surface and the front end surface of the protector fixing portion 3a), while the metal shell 3 is formed of a material (SUS430) that can be subjected to working (crimping or the like) accompanied with deformation. Therefore, the heat resistance of the entire sensor can be improved.

The protector fixing portion 3a, which is a portion, of the metal shell 3, on the front side relative to the protector opposing surface 3b, has a restriction regarding increase in its dimension in the radial direction of the sensor. Therefore, it is difficult to ensure a large thickness from the inner surface of the through-hole 57 to the outer surface of the protector fixing portion 3a opposing the element protector 9. Accordingly, the protector fixing portion 3a is a portion that is likely to be reduced in strength and broken when corrosion or the like occurs due to influence of high temperature, which may result in falling of the element protector 9 in some cases.

In contrast, the gas sensor 1 adopts the structure in which the metal shell protecting member 10 and the element protector 9 cover at least a region, of the protector internal region A1 of the metal shell 3, on the front side relative to the protector opposing surface 3b. Therefore, corrosion of the protector fixing portion 3a of the metal shell 3 due to influence of high temperature is suppressed, thereby suppressing breakage of the metal shell 3.

Therefore, the gas sensor 1 can improve the heat resistance while including the metal shell 3 formed of a material that can be subjected to working accompanied with deformation.

The metal shell protecting member 10 is formed in a tubular shape having the insertion hole 10c through which the detection element 5 is inserted. The metal shell protecting member 10 having such a shape can be disposed inside the through-hole 57 of the metal shell 3, with the detection element 5 being inserted through the insertion hole 10c, and can cover at least a region, of the protector internal region A1, on the front side relative to the protector opposing surface 3b.

The metal shell protecting member 10 includes the flange portion 10b that is in contact with the inner surface of the element protector 9 entirely in the circumferential direction. Providing the flange portion 10b (protector contact portion) suppresses formation of a gap between the metal shell protecting member 10 and the element protector 9, and thus the measurement target (exhaust gas) is suppressed from reaching the metal shell 3 through the outer side of the metal shell protecting member 10.

As described above, since the metal shell protecting member 10 has the flange portion 10b, high-temperature exhaust gas is not likely to be in direct contact with the metal shell 3, thereby further suppressing corrosion of the metal shell 3 due to high temperature, and breakage of the metal shell 3.

The metal shell protecting member 10 is formed of a heat-resistant metal material (NCF601 or SUS310). In this case, the thickness of the metal shell protecting member 10 can be reduced while achieving the same strength, as compared to the case of using a ceramic material.

Thus, a large space can be ensured between the metal shell protecting member 10 and the detection element 5, whereby thermal influence on the detection element 5 by the temperature (amount of heat) of the metal shell protecting member 10 can be suppressed.

The metal shell protecting member 10 is formed of a material superior in corrosion resistance to the metal shell 3. Such a metal shell protecting member 10 is not likely to be corroded by the measurement target (exhaust gas), and suppresses corrosion of the metal shell 3 by the measurement target.

1-4. Correspondence of Terms

A description will be given of the correspondence between terms used in the present embodiment.

The gas sensor 1 corresponds to an example of a sensor, the detection element 5 corresponds to an example of a sensor element, the metal shell 3 corresponds to an example of a metal shell, the element protector 9 corresponds to an example of an element protector, and the ceramic holder 61 and the metal holder 71 correspond to examples of element holding members.

The protector opposing surface 3b corresponds to an example of a protector opposing surface, the protector internal region A1 corresponds to an example of a protector internal region, the metal shell protecting member 10 corresponds to an example of a metal shell protecting member, and the flange portion 10b corresponds to an example of a protector contact portion.

2. Second Embodiment

2-1. Overall Structure

Hereinafter, a second gas sensor 101 according to a second embodiment is described.

The same parts of the second embodiment as those of the first embodiment are designated by the same reference numerals, or explanation thereof will be omitted.

Since the second embodiment is different from the first embodiment in the metal shell protecting member, the metal shell protecting member will be mainly described.

Figure 4:
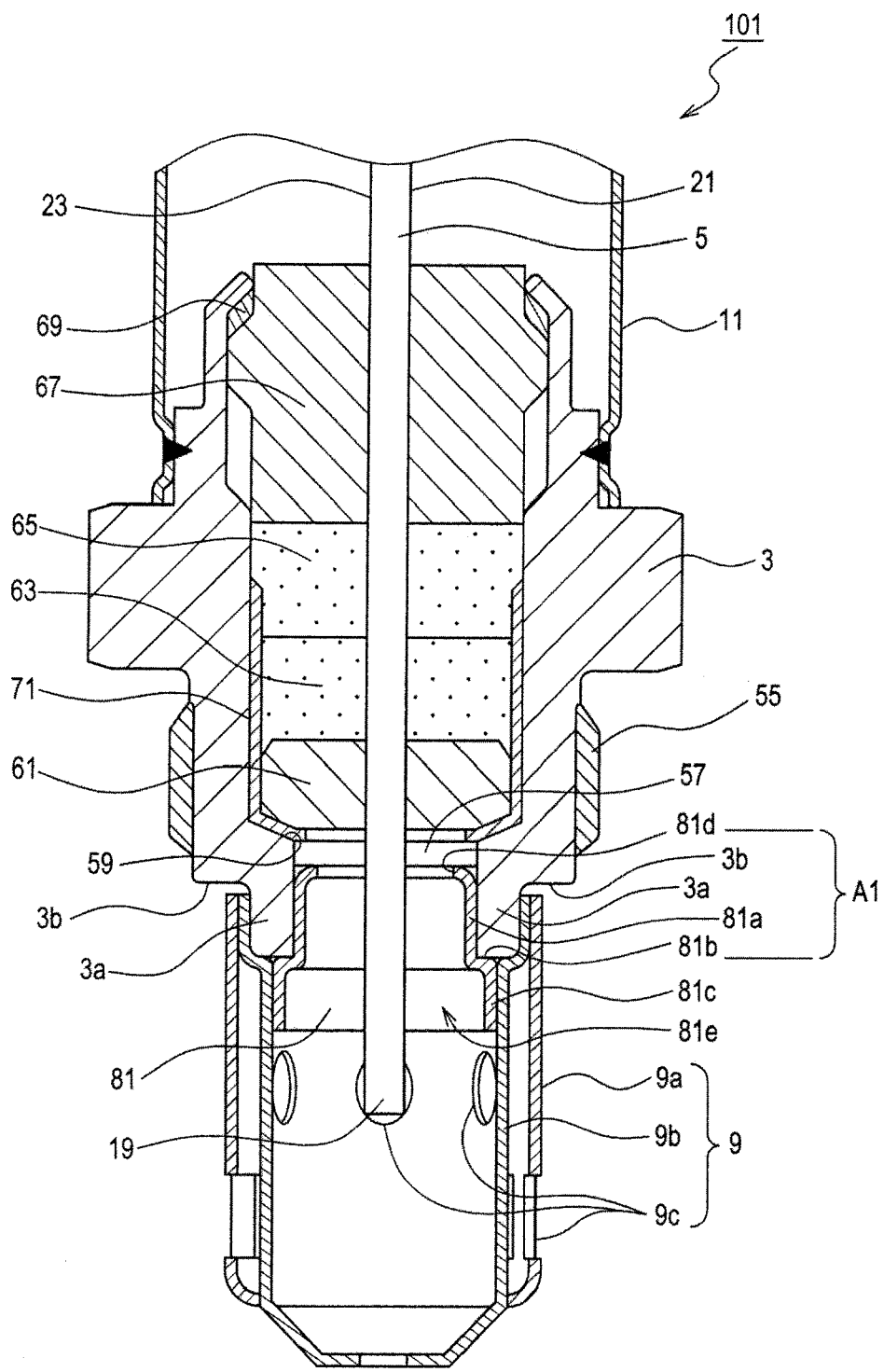
FIG. 4 is a cross-sectional view showing an internal structure of a front-side part of a second gas sensor.

FIG. 4 is a cross-sectional view showing an internal structure of a front-side part of the second gas sensor 101.

In FIG. 4, the downward direction is a direction toward a front end of the gas sensor, and the upward direction is a direction toward a rear end of the gas sensor.

The second gas sensor 101 includes a metal shell 3, a detection element 5, an element protector 9, a second metal shell protecting member 81, an outer casing 11, a ceramic separator 13, and a closing member 15.

Although in FIG. 4 the components (the ceramic separator 13, the closing member 15, etc.) included in a rear-side part of the second gas sensor 101 are not shown, the components in the rear-side part of the second gas sensor 101 are identical to those of the first embodiment.

In the second gas sensor 101, a portion, of the inner protector 9b of the element protector 9, on the front side relative to the front end surface of the protector fixing portion 3a is formed to have a larger diameter perpendicular to the axial direction than in the first embodiment. That is, the dimension of a gap between the outer surface of the inner protector 9b and the inner surface of the outer protector 9a is smaller in the second embodiment than in the first embodiment.

Thus, the inner protector 9b of the second embodiment is disposed so as to cover a part of the front end surface of the protector fixing portion 3a of the metal shell 3. Meanwhile, the inner protector 9b of the first embodiment is disposed so as to cover the entire front end surface of the protector fixing portion 3a of the metal shell 3 (specifically, so as to cover the entire front end surface via the flange portion 10b).

2-2. Second Metal Shell Protecting Member

Figure 5:
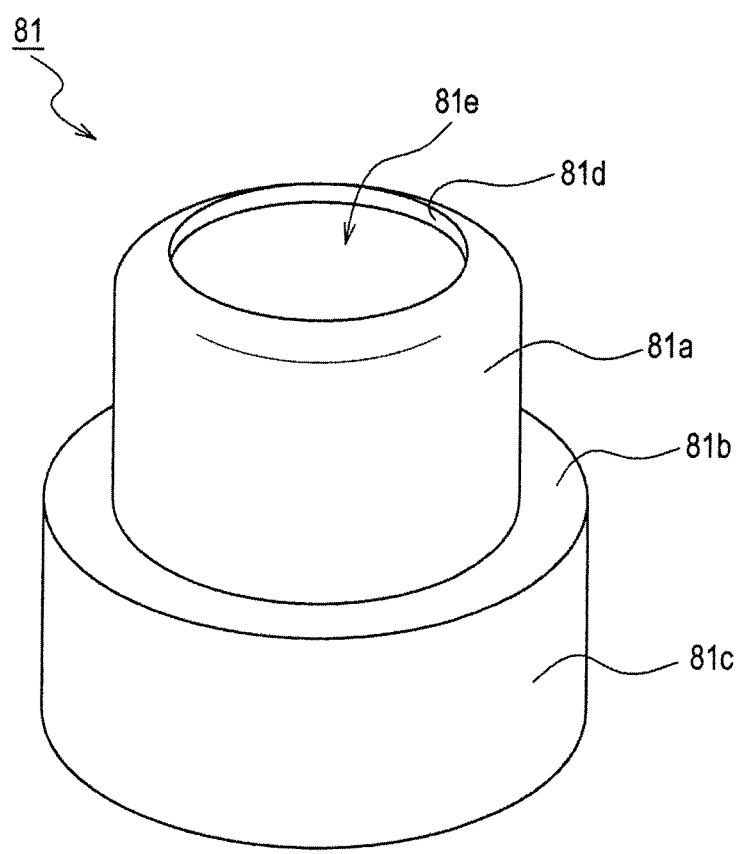
FIG. 5 is a perspective view showing an external appearance of a second metal shell protecting member.

FIG. 5 is a perspective view showing an external appearance of the second metal shell protecting member 81.

The second metal shell protecting member 81 includes a rear-side tubular portion 81a, a step portion 81b, a front-side tubular portion 81c, and an inward projecting portion 81d. In the second metal shell protecting member 81, an insertion hole 81e is formed, which penetrates in the axial direction and through which the detection element 5 is to be inserted. The second metal shell protecting member 81 is formed of a heat-resistant metal material (NCF601 or SUS310).

The rear-side tubular portion 81a is formed in a cylindrical shape in which an outer diameter thereof perpendicular to the axial direction is equal to the inner diameter of the through-hole 57 of the metal shell 3. The front-side tubular portion 81c is formed in a cylindrical shape in which an outer diameter thereof perpendicular to the axial direction is equal to the inner diameter of the element protector 9 (inner protector 9b). Therefore, the outer diameter, perpendicular to the axial direction, of the rear-side tubular portion 81a is smaller than that of the front-side tubular portion 81c.

The step portion 81b is formed so as to connect a front end portion of the rear-side tubular portion 81a to a rear end portion of the front-side tubular portion 81c.

The inward projecting portion 81d is formed so as to project inward in the circumferential direction, at a rear end portion of the rear-side tubular portion 81a.

As shown in FIG. 4, the second metal shell protecting member 81 is disposed at the front end portion of the metal shell 3 such that the rear-side tubular portion 81a is in contact with the front-side inner surface of the through-hole 57 of the metal shell 3, the step portion 81b is in contact with the front end surface of the metal shell 3, and the front-side tubular portion 81c is in contact with the inner surface of the element protector 9 (specifically, the inner protector 9b) entirely in the circumferential direction.

As in the first embodiment, the metal shell 3 is formed of SUS430, and includes a protector fixing portion 3a and a protector opposing surface 3b.

The second metal shell protecting member 81 is disposed so as to cover at least a region, of the protector internal region A1 of the metal shell 3, on the front side relative to the protector opposing surface 3b (in other words, a region corresponding to the inner surface of the protector fixing portion 3a and a part of the front end surface thereof). Specifically, the rear-side tubular portion 81a of the second metal shell protecting member 81 covers a region, of the inner surface of the through-hole 57, on the front side relative to the protector opposing surface 3b, and the step portion 81b of the second metal shell protecting member 81 covers a part of the front end surface of the protector fixing portion 3a. Therefore, at least a region, of the protector internal region A1, on the front side relative to the protector opposing surface 3b is covered with the second metal shell protecting member 81 and the element protector 9.

The heat-resistant metal material (NCF601 or SUS310) forming the second metal shell protecting member 81 is superior in heat resistance and corrosion resistance to the material (SUS430) forming the metal shell 3.

2-3. Effects

As described above, the second gas sensor 101 according to the present embodiment is provided with the second metal shell protecting member 81 that is formed of a material superior in heat resistance to the metal shell 3, whereby a high-temperature measurement target (exhaust gas) is prevented from being in direct contact with a region, of the protector internal region A1 of the metal shell 3, on the front side relative to the protector opposing surface 3b.

That is, in the second gas sensor 101, it is possible to suppress corrosion due to high temperature, of a region, of the protector internal region A1 of the metal shell 3, on the front end side relative to the protector opposing surface 3b (i.e., the inner surface and the front end surface of the protector fixing portion 3a), while the metal shell 3 is formed of a material (SUS430) that can be subjected to working (crimping or the like) accompanied with deformation. Therefore, the heat resistance of the entire sensor can be improved.

The second metal shell protecting member 81 includes the front-side tubular portion 81c that is in contact with the inner surface of the element protector 9 entirely in the circumferential direction. Providing the front-side tubular portion 81c (protector contact portion) suppresses formation of a gap between the second metal shell protecting member 81 and the element protector 9, and thus the measurement target (exhaust gas) is suppressed from reaching the metal shell 3 through the outer side of the second metal shell protecting member 81.

The second metal shell protecting member 81 has, on the rear side thereof, the inward projecting portion 81d that projects inward.

Since the second metal shell protecting member 81 has the inward projecting portion 81d, the exhaust gas that moves in the second metal shell protecting member 81 toward the rear end of the protecting member 81 collides against the inward projecting portion 81d, whereby the moving direction of the exhaust gas can be changed. Thus, the exhaust gas is suppressed from reaching the metal shell 3 through the inner side of the second metal shell protecting member 81.

As described above, since the second metal shell protecting member 81 has the inward projecting portion 81d, the exhaust gas is not likely to be in direct contact with the metal shell 3, thereby further suppressing corrosion of the metal shell 3 due to high temperature, and breakage of the metal shell 3.

2-4. Correspondence of Terms

A description will be given of the correspondence between terms used in the present embodiment.

The second gas sensor 101 corresponds to an example of a sensor, the element protector 9 corresponds to an example of an element protector, the second metal shell protecting member 81 corresponds to an example of a metal shell protecting member, the front-side tubular portion 81c corresponds to an example of a protector contact portion, and the inward projecting portion 81d corresponds to an example of an inward projecting portion.

3. Third Embodiment 3-1. Overall Structure

Next, a third gas sensor 103 according to a third embodiment will be described.

The same parts of the third embodiment as those of the first embodiment are designated by the same reference numerals, or explanation thereof will be omitted.

Figure 6:
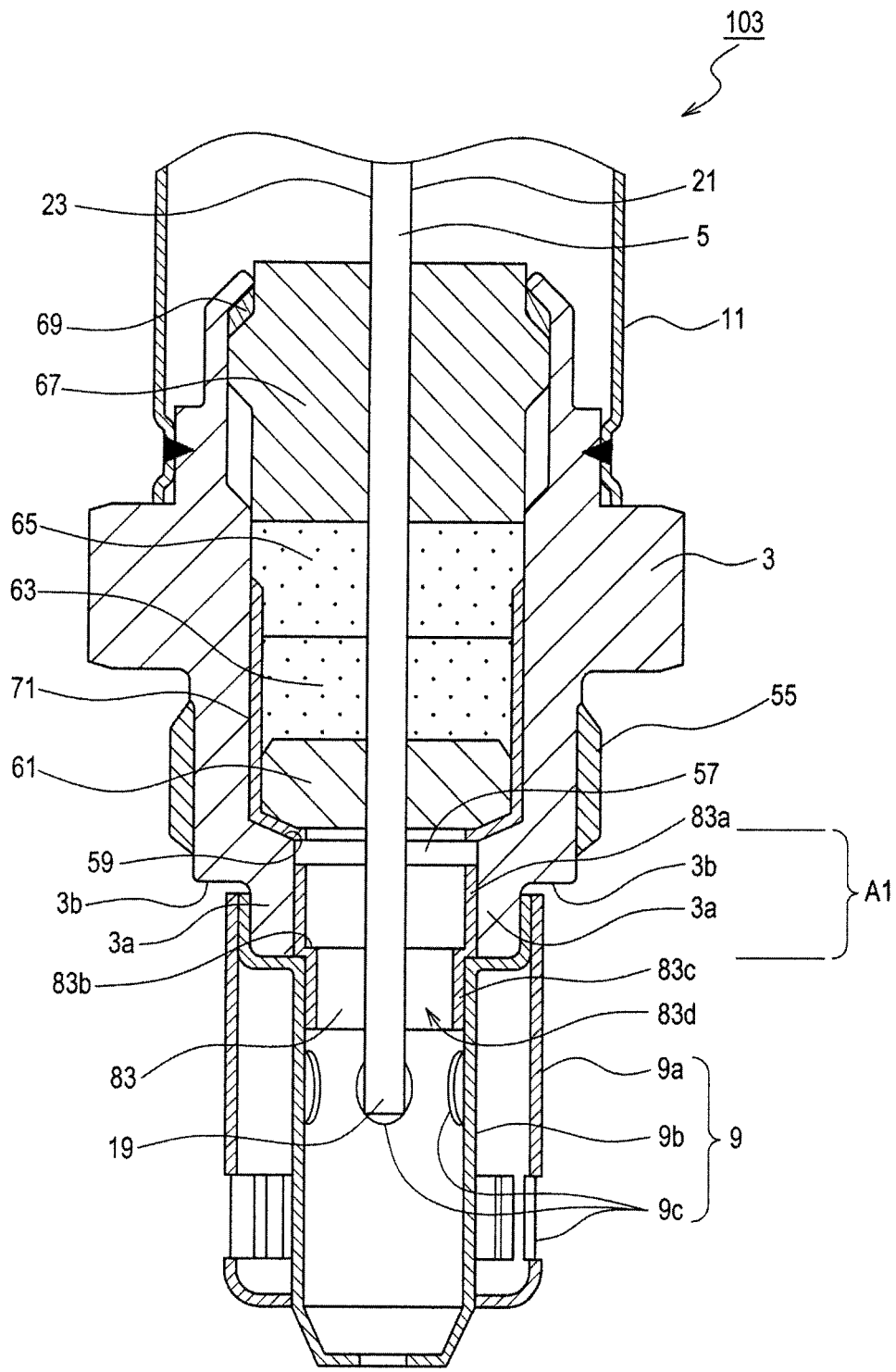
FIG. 6 is a cross-sectional view showing an internal structure of a front-side part of a third gas sensor.

FIG. 6 is a cross-sectional view showing an internal structure of a front-side part of the third gas sensor 103.

In FIG. 6, the downward direction is a direction toward a front end of the gas sensor, and the upward direction is a direction toward a rear end of the gas sensor.

The third gas sensor 103 includes a metal shell 3, a detection element 5, an element protector 9, a third metal shell protecting member 83, an outer casing 11, a ceramic separator 13, and a closing member 15.

Although in FIG. 6 the components (the ceramic separator 13, closing member 15, etc.) included in a rear-side part of the third gas sensor 103 are not shown, the components in the rear-side part of the third gas sensor 103 are identical to those of the first embodiment.

In the third gas sensor 103, a portion, of the inner protector 9b of the element protector 9, on the front side relative to the front end surface of the protector fixing portion 3a is formed to have a smaller diameter perpendicular to the axial direction than in the first embodiment. That is, the dimension of a gap between the outer surface of the inner protector 9b and the inner surface of the outer protector 9a is larger in the third embodiment than in the first embodiment.

Thus, the inner protector 9b of the third embodiment is disposed so as to cover a portion of a front-side opening of the through-hole 57 of the metal shell 3 (specifically, so as to cover a portion of the front-side opening via the third metal shell protecting member 83). Meanwhile, the inner protector 9b of the first embodiment is disposed so as not to cover a front-side opening of the through-hole 57 of the metal shell 3.

3-2. Third Metal Shell Protecting Member

Figure 7:
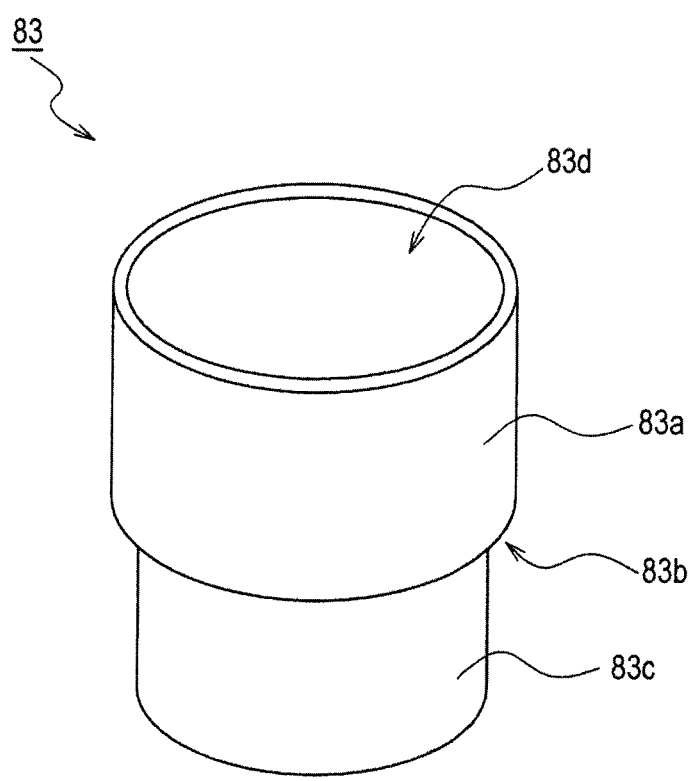
FIG. 7 is a perspective view showing an external appearance of a third metal shell protecting member.

FIG. 7 is a perspective view showing an external appearance of the third metal shell protecting member 83.

The third metal shell protecting member 83 includes a rear-side tubular portion 83a, a step portion 83b, and a front-side tubular portion 83c. In the third metal shell protecting member 83, an insertion hole 83d is formed, which penetrates in the axial direction and through which the detection element 5 is to be inserted. The third metal shell protecting member 83 is formed of a heat-resistant metal material (NCF601 or SUS310).

The rear-side tubular portion 83a is formed in a cylindrical shape in which an outer diameter thereof perpendicular to the axial direction is equal to the inner diameter of the through-hole 57 of the metal shell 3. The front-side tubular portion 83c is formed in a cylindrical shape in which an outer diameter thereof perpendicular to the axial direction is equal to the inner diameter of the element protector 9 (inner protector 9b). Therefore, the outer diameter of the rear-side tubular portion 83a, perpendicular to the axial direction, is larger than that of the front-side tubular portion 83c.

The step portion 83b is formed so as to connect a front end portion of the rear-side tubular portion 83a to a rear end portion of the front-side tubular portion 83c.

As shown in FIG. 6, the third metal shell protecting member 83 is disposed at the front end portion of the metal shell 3 such that the rear-side tubular portion 83a is in contact with the front-side inner surface of the through-hole 57 of the metal shell 3, and the front-side tubular portion 83c is in contact with the inner surface of the element protector 9 (specifically, the inner protector 9b) entirely in the circumferential direction.

As in the first embodiment, the metal shell 3 is formed of SUS430, and includes a protector fixing portion 3a and a protector opposing surface 3b.

The third metal shell protecting member 83 is disposed so as to cover at least a region, of the protector internal region A1 of the metal shell 3, on the front side relative to the protector opposing surface 3b (in other words, a region corresponding to the inner surface of the protector fixing portion 3a). Specifically, the rear-side tubular portion 83a of the third metal shell protecting member 83 covers a region, of the inner surface of the through-hole 57, on the front side relative to the protector opposing surface 3b. Further, the inner protector 9b covers the entire front end surface of the protector fixing portion 3a of the metal shell 3. Therefore, at least a region, of the protector internal region A1, on the front side relative to the protector opposing surface 3b is covered with the third metal shell protecting member 83 and the inner protector 9b.

The heat-resistant metal material (NCF601 or SUS310) forming the third metal shell protecting member 83 is superior in heat resistance and corrosion resistance to the material (SUS430) forming the metal shell 3.

3-3. Effects

As described above, the third gas sensor 103 according to the present embodiment is provided with the third metal shell protecting member 83 that is formed of a material superior in heat resistance to the metal shell 3, whereby a high-temperature measurement target (exhaust gas) is prevented from being in direct contact with a region, of the protector internal region A1 of the metal shell 3, on the front side relative to the protector opposing surface 3b.

That is, in the third gas sensor 103, it is possible to suppress corrosion due to high temperature, of a region, of the protector internal region A1 of the metal shell 3, on the front side relative to the protector opposing surface 3b (the inner surface and the front end surface of the protector fixing portion 3a), while the metal shell 3 is formed of a material (SUS430) that can be subjected to working (crimping or the like) accompanied with deformation. Therefore, the heat resistance of the entire sensor can be improved.

The third metal shell protecting member 83 includes the front-side tubular portion 83c that is in contact with the inner surface of the element protector 9 entirely in the circumferential direction. Providing the front-side tubular portion 83c (protector contact portion) suppresses formation of a gap between the third metal shell protecting member 83 and the element protector 9, and thus the measurement target (exhaust gas) is suppressed from reaching the metal shell 3 through the outer side of the third metal shell protecting member 83.

3-4. Correspondence of Terms

A description will be given of the correspondence between terms used in the present embodiment.

The third gas sensor 103 corresponds to an example of a sensor, the element protector 9 corresponds to an example of an element protector, the third metal shell protecting member 83 corresponds to an example of a metal shell protecting member, and the front-side tubular portion 83c corresponds to an example of a protector contact portion.

4. Fourth Embodiment

4-1. Overall Structure

Next, a fourth gas sensor 105 according to a fourth embodiment will be described.

The same parts of the fourth embodiment as those of the first embodiment are designated by the same reference numerals, or explanation thereof will be omitted.

Figure 8:
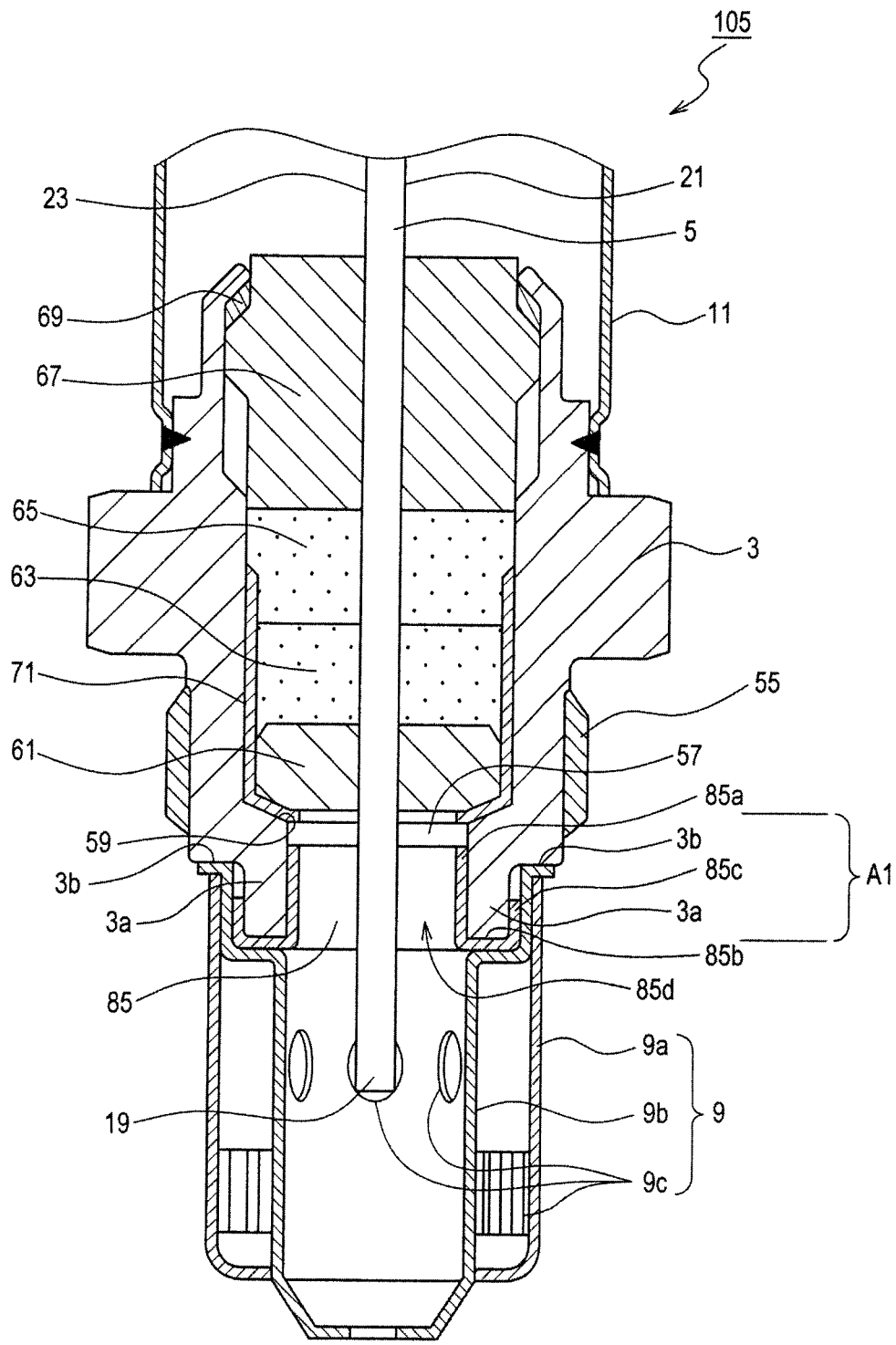
FIG. 8 is a cross-sectional view showing an internal structure of a front-side part of a fourth gas sensor.

FIG. 8 is a cross-sectional view showing an internal structure of a front-side part of the fourth gas sensor 105.

In FIG. 8, the downward direction is a direction toward a front end of the gas sensor, and the upward direction is a direction toward a rear end of the gas sensor.

The fourth gas sensor 105 includes a metal shell 3, a detection element 5, an element protector 9, a fourth metal shell protecting member 85, an outer casing 11, a ceramic separator 13, and a closing member 15.

Although in FIG. 8 the components (the ceramic separator 13, closing member 15, etc.) included in a rear-side part of the fourth gas sensor 105 are not shown, the components in the rear-side part of the fourth gas sensor 105 are identical to those of the first embodiment.

In the fourth gas sensor 105, a portion, of the element protector 9 (the outer protector 9a and the inner protector 9b), surrounding the protector fixing portion 3a of the metal shell 3 is formed to have a larger diameter perpendicular to the axial direction than in the first embodiment.

Thus, the element protector 9 of the fourth embodiment is fixed to the protector fixing portion 3a via the fourth metal shell protecting member 85 by welding or the like.

4-2. Fourth Metal Shell Protecting Member

Figure 9:
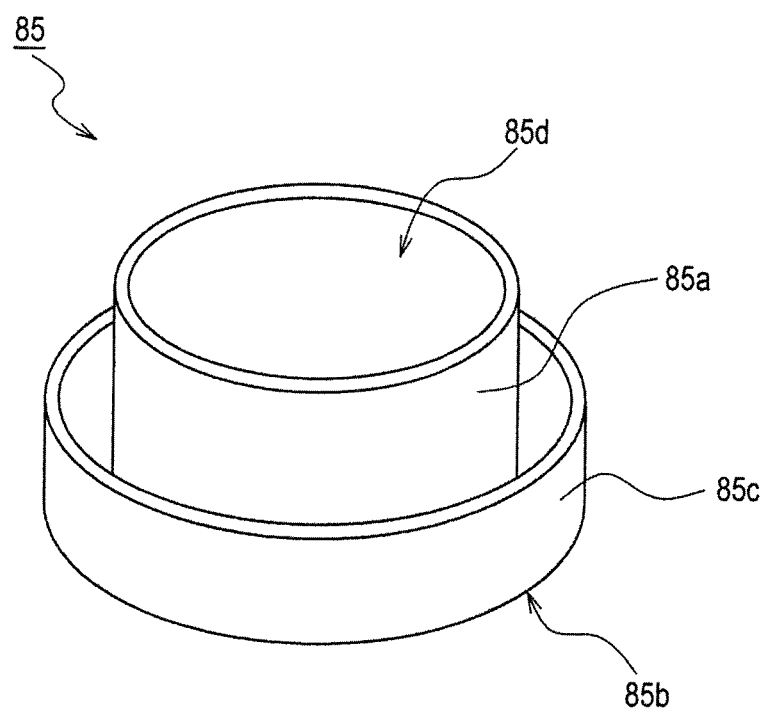
FIG. 9 is a perspective view showing an external appearance of a fourth metal shell protecting member.

FIG. 9 is a perspective view showing an external appearance of the fourth metal shell protecting member 85.

The fourth metal shell protecting member 85 includes an inner-side tubular portion 85a, a connecting portion 85b, and an outer-side tubular portion 85c. In the inner-side tubular portion 85a, an insertion hole 85d is formed, which penetrates in the axial direction and through which the detection element 5 is to be inserted. The fourth metal shell protecting member 85 is formed of a heat-resistant metal material (NCF601 or SUS310).

The inner-side tubular portion 85a is formed in a cylindrical shape in which an outer diameter thereof perpendicular to the axial direction is equal to the inner diameter of the through-hole 57 of the metal shell 3. The outer-side tubular portion 85c is formed in a cylindrical shape in which an inner diameter thereof perpendicular to the axial direction is equal to the outer diameter of the protector fixing portion 3a of the metal shell 3.

The connecting portion 85b is formed so as to connect a front end portion of the inner-side tubular portion 85a to a front end portion of the outer-side tubular portion 85c.

As shown in FIG. 8, the fourth metal shell protecting member 85 is disposed at the front end portion of the metal shell 3 such that the inner-side tubular portion 85a is in contact with the front-side inner surface of the through-hole 57 of the metal shell 3, the connecting portion 85b is in contact with the front end surface of the protector fixing portion 3a, and the outer-side tubular portion 85c is in contact with an outer peripheral surface of the protector fixing portion 3a. The connecting portion 85b and the outer-side tubular portion 85c each are in contact with the inner surface of the element protector 9 (specifically, the inner protector 9b) entirely in the circumferential direction.

As in the first embodiment, the metal shell 3 is formed of SUS430, and includes a protector fixing portion 3a and a protector opposing surface 3b.

The fourth metal shell protecting member 85 is disposed so as to cover at least a region, of the protector internal region A1 of the metal shell 3, on the front side relative to the protector opposing surface 3b (in other words, a region corresponding to the inner surface and the front end surface of the protector fixing portion 3a). Specifically, of the fourth metal shell protecting member 85, the inner-side tubular portion 85a covers a region, of the inner surface of the through-hole 57, on the front side relative to the protector opposing surface 3b, the connecting portion 85b covers the front end surface of the protector fixing portion 3a, and the outer-side tubular portion 85c covers a partial region of the outer surface of the protector fixing portion 3a. Therefore, at least a region, of the protector internal region A1, on the front side relative to the protector opposing surface 3*b* is covered with the fourth metal shell protecting member 85 and the inner protector 9*b*.

The heat-resistant metal material (NCF601 or SUS310) forming the fourth metal shell protecting member 85 is superior in heat resistance and corrosion resistance to the material (SUS430) forming the metal shell 3.

4-3. Effects

As described above, the fourth gas sensor 105 according to the present embodiment is provided with the fourth metal shell protecting member 85 that is formed of a material superior in heat resistance to the metal shell 3, whereby a high-temperature measurement target (exhaust gas) is prevented from being in direct contact with a region, of the protector internal region A1 of the metal shell 3, on the front side relative to the protector opposing surface 3*b*.

That is, in the fourth gas sensor 105, it is possible to suppress corrosion due to high temperature, of a region, of the protector internal region A1 of the metal shell 3, on the front side relative to the protector opposing surface 3*b* (i.e., the inner surface and the front end surface of the protector fixing portion 3*a*), while the metal shell 3 is formed of a material (SUS430) that can be subjected to working (crimping or the like) accompanied with deformation. Therefore, the heat resistance of the entire sensor can be improved.

The fourth metal shell protecting member 85 includes the connecting portion 85*b* and the outer-side tubular portion 85*c* that are in contact with the inner surface of the element protector 9 entirely in the circumferential direction. Providing the connecting portion 85*b* and the outer-side tubular portion 85*c* (protector contact portion) suppresses formation of a gap between the fourth metal shell protecting member 85 and the element protector 9, and thus the measurement target (exhaust gas) is suppressed from reaching the metal shell 3 through the outer side of the fourth metal shell protecting member 85.

4-4. Correspondence of Terms

A description will be given of the correspondence between terms used in the present embodiment.

The fourth gas sensor 105 corresponds to an example of a sensor, the element protector 9 corresponds to an example of an element protector, the fourth metal shell protecting member 85 corresponds to an example of a metal shell protecting member, and the connecting portion 85*b* and the outer-side tubular portion 85*c* correspond to an example of a protector contact portion.

5. Fifth Embodiment

Figure 10:
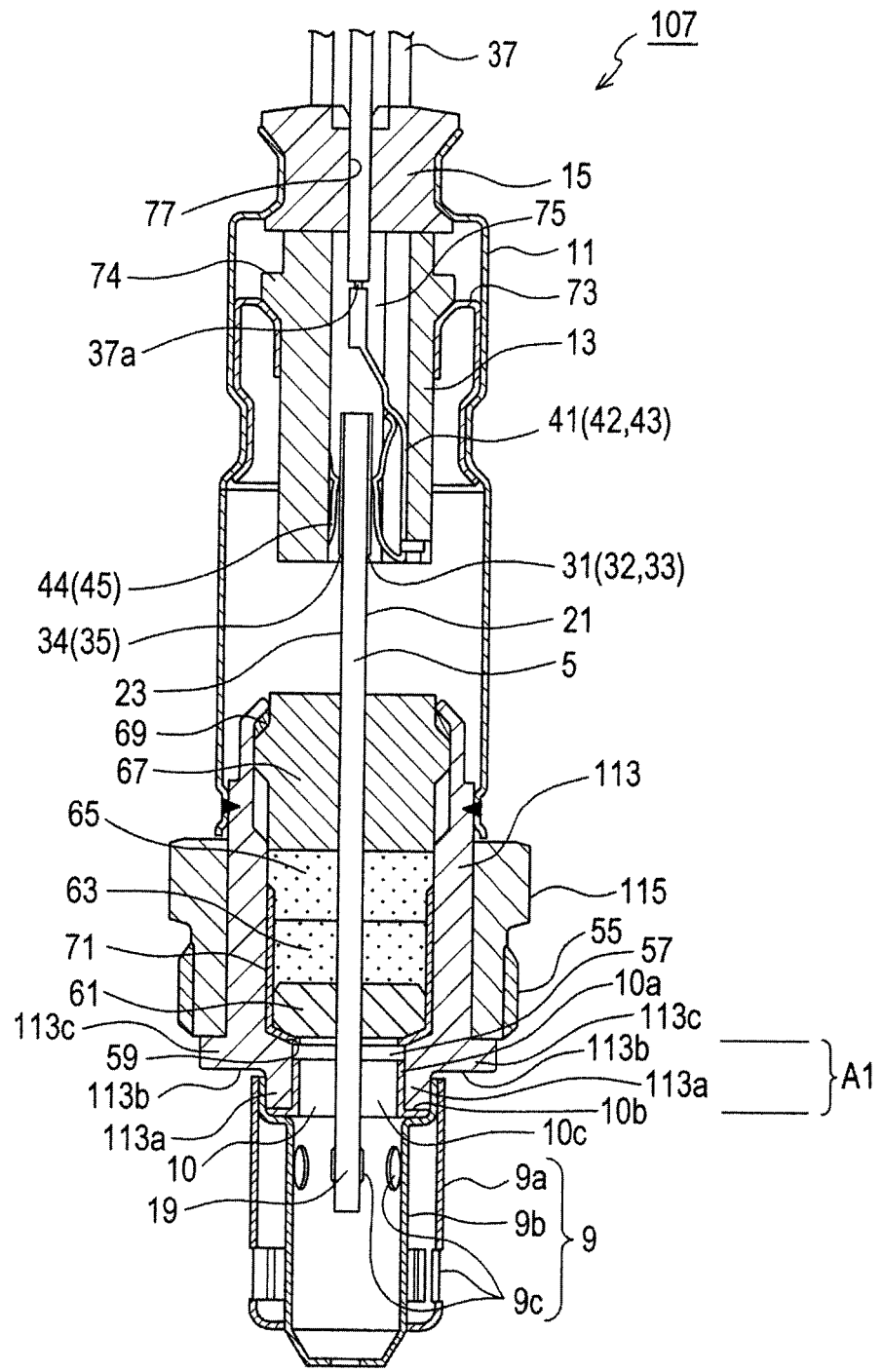
FIG. 10 is a cross-sectional view showing an overall structure of a fifth gas sensor.

While in the above embodiments the sensor that includes the metal shell 3 integrated with the screw portion 55 has been described, the present invention is not limited to the sensor including the metal shell having this structure. For example, a fifth gas sensor 107 according to a fifth embodiment shown in FIG. 10 may be adopted, which includes a second metal shell 113 fixed to a sensor mount position by means of an attachment member 115 having a screw portion 55.

The same parts of the fifth gas sensor 107 as those of the gas sensor 1 of the first embodiment are designated by the same reference numerals, or explanation thereof will be omitted.

The second metal shell 113 is a tubular member having, at an axial center thereof, a through-hole 57 penetrating in the axial direction. The second metal shell 113 includes, at a front end portion thereof, a flange portion 113*c* projecting radially outward. In the through-hole 57, a shelf portion 59 projecting radially inward is formed. The second metal shell 113 is formed of a metal material (e.g., stainless steel (SUS430) or the like).

The second metal shell 113 includes a protector fixing portion 113*a* for fixing the element protector 9 to a front end thereof. The protector fixing portion 113*a* is formed to have a thickness (a dimension from an inner surface thereof facing the through-hole 57 to an outer surface thereof being in contact with the element protector 9) smaller than the thickness of the flange portion 113*c* of the second metal shell 113.

The second metal shell 113 has a protector opposing surface 113*b* at an outer surface thereof. The protector opposing surface 113*b* is formed so as to oppose the rear end portion of the element protector 9 fixed to the protector fixing portion 113*a*. The protector opposing surface 3*b* according to the present embodiment is formed as a plane perpendicular to the axial direction (in other words, a plane opposing the front end) at a portion, of the outer surface of the metal shell 3, on the front side relative to the flange portion 113*c*.

The attachment member 115 is disposed on the outer periphery of the second metal shell 113 on the rear side relative to the flange portion 113*c* of the second metal shell 113, and is formed to be rotatable with respect to the second metal shell 113. On an outer surface of the attachment member 115, a screw portion (external thread portion) 55 is formed, which is screwed to the sensor mount position. The attachment member 115 applies a frontward pressing force to the flange portion 113*c* of the second metal shell 113 when the screw portion 55 is screwed to the sensor mount position.

That is, the second metal shell 113 is fixed to the sensor mount position when the flange portion 113*c* is pressed frontward by the pressing force from the attachment member 115.

Also in the fifth gas sensor 107 having the second metal shell 113 of the above structure, the same effects as those of the first embodiment can be achieved by providing the metal shell protecting member 10, whereby the heat resistance can be improved while including the second metal shell 113 formed of a material that can be subjected to working accompanied with deformation.

The fifth gas sensor 107 corresponds to an example of a sensor, and the second metal shell 113 corresponds to an example of a metal shell.

6. Sixth Embodiment

Figure 11:
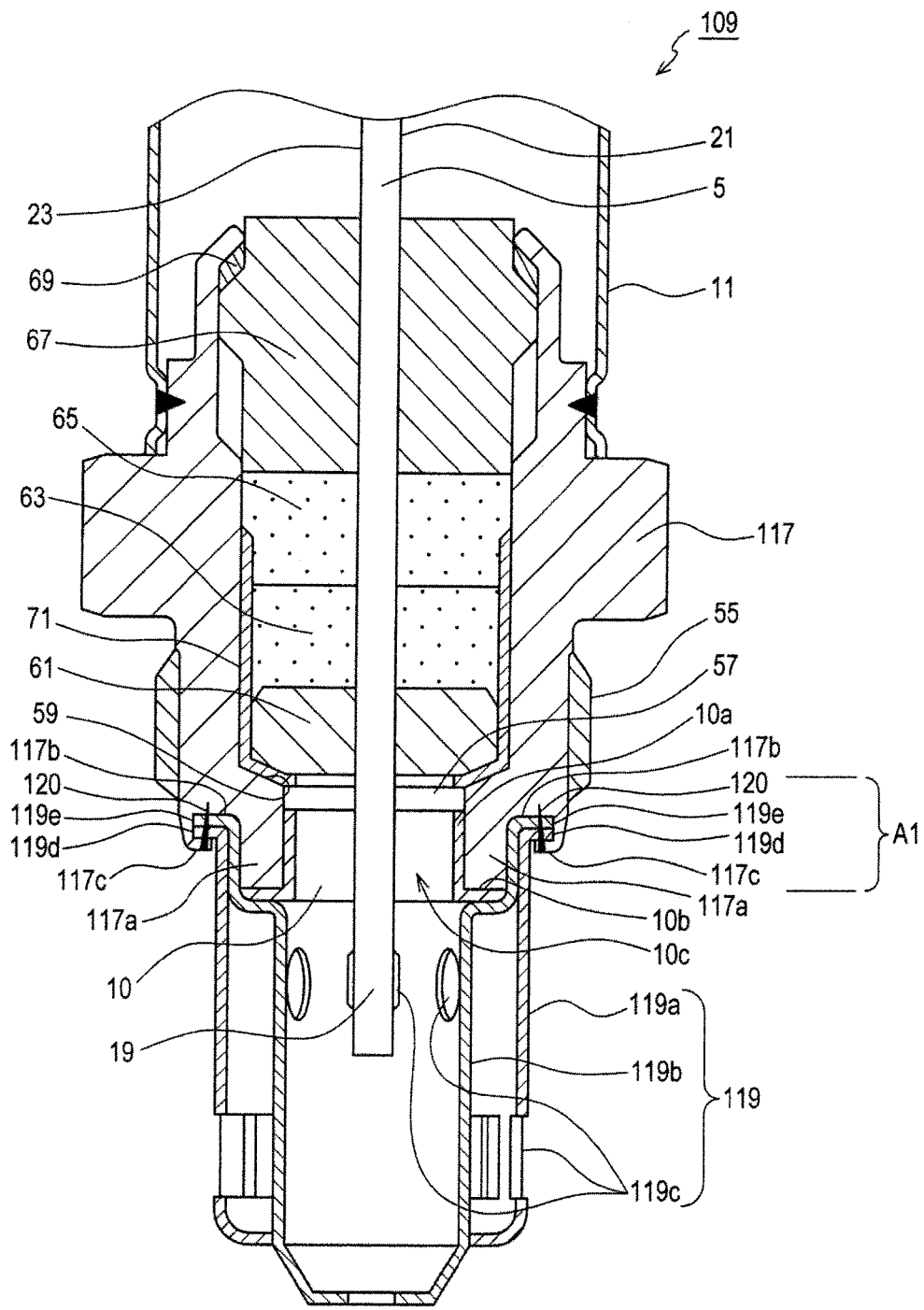
FIG. 11 is a cross-sectional view showing an internal structure of a front-side part of a sixth gas sensor.

While in the above embodiments the sensor that adopts welding as a method for fixing the element protector to the metal shell has been described, the fixing method is not limited to welding. For example, a sixth gas sensor 109 shown in FIG. 11 may be adopted, in which the element protector is fixed to the metal shell by crimping of the metal shell, in addition to welding.

The same parts of the sixth gas sensor 109 as those of the gas sensor 1 of the first embodiment are designated by the same reference numerals, or explanation thereof will be omitted.

The sixth gas sensor 109 includes a third metal shell 117 and a second element protector 119.

The third metal shell 117 is a tubular member that includes, at an outer surface thereof, a screw portion 55 for fixing the third metal shell 117 to the exhaust pipe, and includes a through-hole 57 at an axial center thereof. In the through-hole 57, a shelf portion 59 projecting radially inward is formed. The third metal shell 117 is formed of a metal material (e.g., stainless steel (SUS430) or the like).

The third metal shell 117 includes: a protector fixing portion 117a and a crimping fixing portion 117c for fixing the second element protector 119 to the front end thereof; and a protector opposing surface 117b which opposes a rear end portion of the second element protector 119.

The protector fixing portion 117a is formed to have a thickness (a dimension from an inner surface thereof facing the through-hole 57 to an outer surface thereof being in contact with the second element protector 119) smaller than the thickness of the screw portion 55 of the third metal shell 117. The protector opposing surface 117b is formed as a plane perpendicular to the axial direction (in other words, a plane opposing the front side) at a portion, of the outer surface of the third metal shell 117, on the front side relative to the screw portion 55.

The crimping fixing portion 117c is formed so as to project frontward from a portion, of the third metal shell 117, outside the protector opposing surface 117b. The crimping fixing portion 117c, before crimping, is formed such that the dimension of a gap between the protector fixing portion 117a and the crimping fixing portion 117c (the dimension of the gap perpendicular to the axial direction) is equal to or larger than the width of the protector opposing surface 117b. When the crimping fixing portion 117c having the above shape is crimped radially inward, the rear end portion (an outer bent portion 119d and an inner bent portion 119e described later) is sandwiched and held between the protector opposing surface 117b and the crimping fixing portion 117c.

The second element protector 119 is a tubular member that is attached to the front-side outer periphery of the third metal shell 117 by welding or the like so as to cover the projecting portion of the detection element 5. The second element protector 119 is formed by using a heat resistance material (e.g., NCF601 or the like). The second element protector 119 has a double structure including a second outer protector 119a and a second inner protector 119b. A plurality of holes 119c, which allow gas to pass therethrough, are formed at, for example, a side wall of the second element protector 119. In addition, the second outer protector 119a and the second inner protector 119b have, at the rear end portions thereof, an outer bent portion 119d and an inner bent portion 119e that are bent radially outward, respectively.

The outer bent portion 119d and the inner bent portion 119e, of the second element protector 119 having the above structure, are disposed between the protector fixing portion 117a of the third metal shell 117 and the crimping fixing portion 117c of the third metal shell 117 before crimping, and thereafter, the crimping fixing portion 117c is crimped radially inward, whereby the second element protector 119 is sandwiched and held between the protector opposing surface 117b and the crimping fixing portion 117c. Thereafter, the crimping fixing portion 117c, the outer bent portion 119d, the inner bent portion 119e, and the protector opposing surface 117b are welded to each other to form a welded portion 120, thereby completing the working to fix the second element protector 119 to the third metal shell 117.

Also in the sixth gas sensor 109 including the third metal shell 117 and the second element protector 119, the same effects as those of the first embodiment can be achieved by providing the metal shell protecting member 10, whereby the heat resistance can be improved while including the third metal shell 117 formed of a material that can be subjected to working accompanied with deformation.

The sixth gas sensor 109 corresponds to an example of a sensor, the third metal shell 117 corresponds to an example of a metal shell, and the second element protector 119 corresponds to an example of an element protector.

7. Seventh Embodiment

Figure 12:
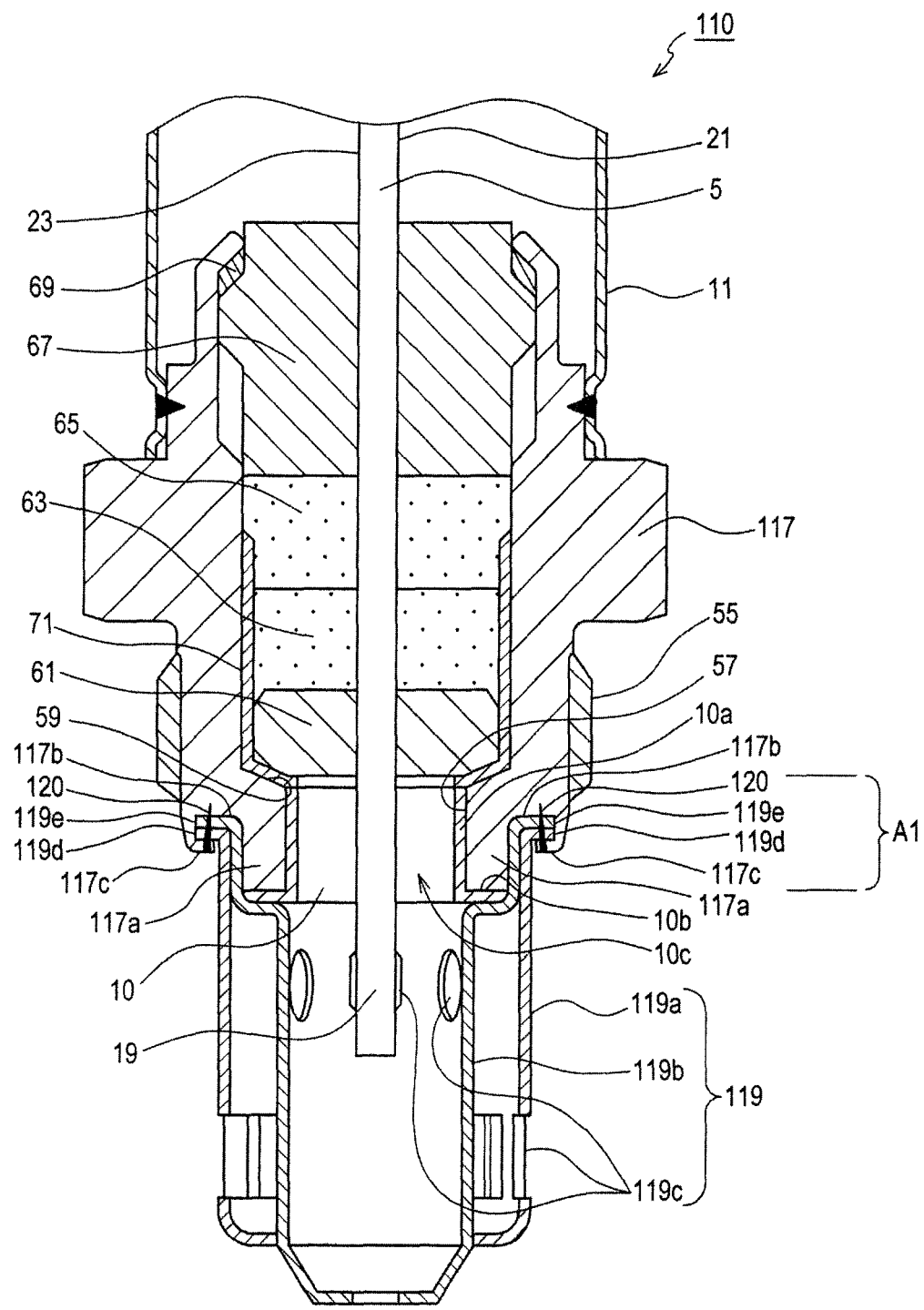
FIG. 12 is a cross-sectional view showing an internal structure of a front-side part of a seventh gas sensor.

In the sensor according to any of the above embodiments, at least a portion of the inner surface of the through-hole in the metal shell (specifically, at least a portion, of the inner surface of the through-hole, on the front side relative to the element holding member (the ceramic holder 61 and the metal holder 71)) is exposed to the measurement target. However, the sensor of the present invention is not limited to the above structure. For example, a seventh gas sensor 110 shown in FIG. 12 may be adopted, in which the tubular portion 10a of the metal shell protecting member 10 covers a region, of the inner surface of the through-hole 57, on the front side relative to the metal holder 71.

The same parts of the seventh gas sensor 110 as those of the gas sensor 109 of the sixth embodiment are designated by the same reference numerals, or explanation thereof will be omitted.

The seventh gas sensor 110 is different from the sixth gas sensor 109 in that the tubular portion 10a of the metal shell protecting member 10 is longer than that of the sixth gas sensor 109, and the rear end of the tubular portion 10a is in contact with the metal holder 71 over the entire circumference. That is, in the seventh gas sensor 110, the metal shell protecting member 10 covers a region, of the inner surface of the through-hole 57, on the front side relative to the metal holder 71, and is contact with the metal holder 71.

Since the seventh gas sensor 110 includes the metal shell protecting member 10 of the above structure, the inner surface of the through-hole 57 is prevented from being in direct contact with the exhaust gas, thereby suppressing corrosion of the third metal shell 117 due to the exhaust gas. Thus, falling of a part of the third metal shell 117 due to corrosion is suppressed, and attachment of chips of the third metal shell 117, which have fallen off due to corrosion, to the detection element 5 is suppressed, thereby suppressing occurrence of an error in a sensor output due to the chips.

Also in the seventh gas sensor 110, the same effects as those of the first embodiment can be achieved by providing the metal shell protecting member 10, whereby the heat resistance can be improved while including the third metal shell 117 formed of a material that can be subjected to working accompanied with deformation.

8. Other Embodiments

While the embodiments of the present invention have been described above, the present invention is not limited to the above embodiments, and may be embodied in various other forms without departing from the scope of the invention.

For example, in the above embodiments, the metal shell protecting member is formed of NCF601 or SUS310. However, the material of the metal shell protecting member is not limited thereto, and other materials superior in heat resistance to the metal shell (e.g., SUS304, SUS316, other heat-resistant metal materials, ceramic materials, etc.) may be adopted.

In the above embodiments, the metal shell is formed of stainless steel (SUS430) and the element protector is formed of NCF601. However, the metal shell and the element protector are not limited to those formed of the above materials, and may be formed by using other metal materials.

Further, the metal shell protecting member provided in the sensors according to the fifth embodiment and the sixth embodiment is not limited to the metal shell protecting member 10 according to the first embodiment. Any of the second metal shell protecting member 81, the third metal shell protecting member 83, and the fourth metal shell protecting member 85 may be used.

The metal shell protecting member including the inward projecting portion is not limited to the second metal shell protecting member 81. The inward projecting portion may be provided in any of the metal shell protecting member 10, the third metal shell protecting member 83, and the fourth metal shell protecting member 85.

Figure 13:
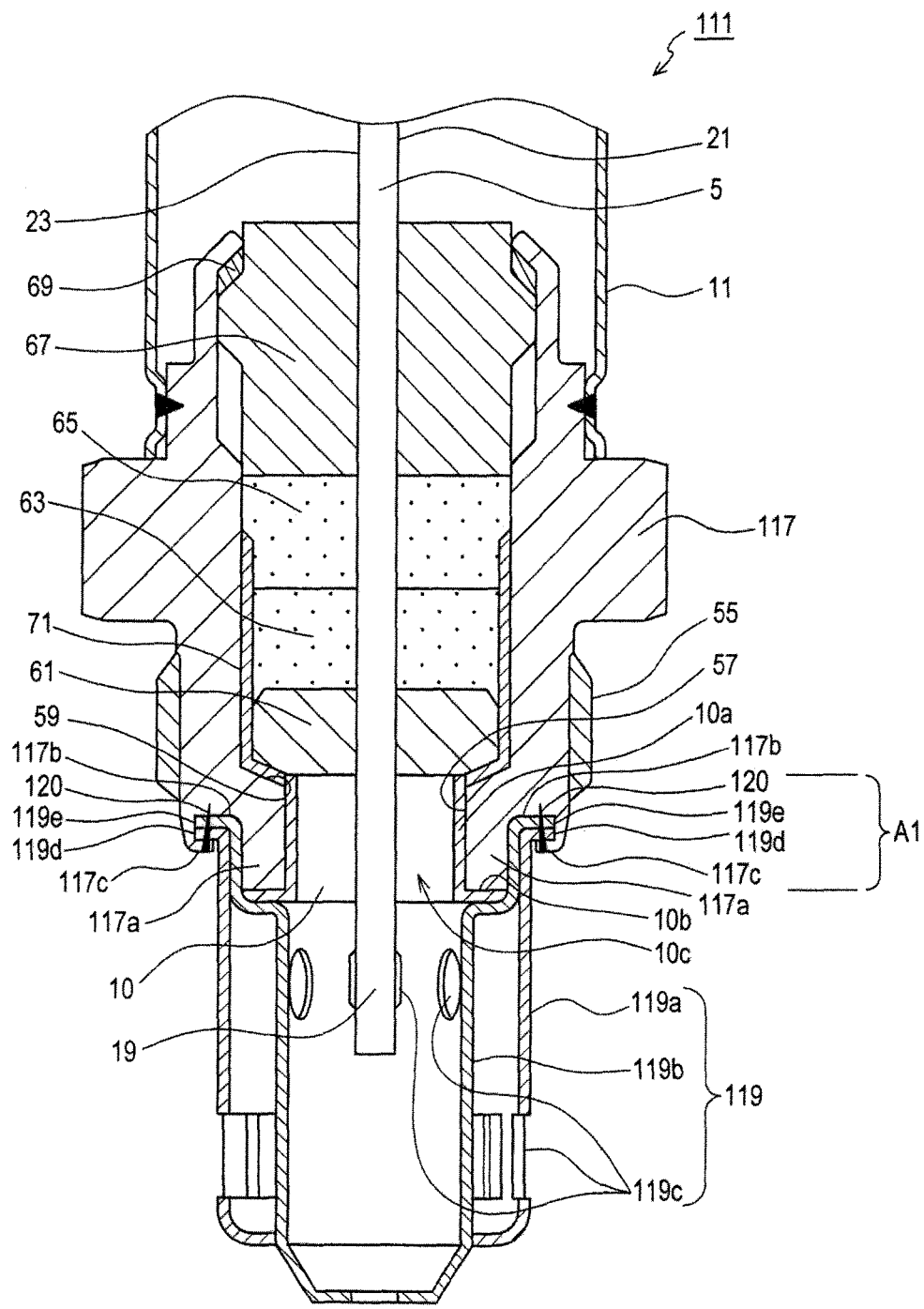
FIG. 13 is a cross-sectional view showing an internal structure of a front-side part of an eighth gas sensor.

The sensor structure, in which a region, of the inner surface of the through-hole in the metal shell, on the front side relative to the element holding member is covered with another member, is not limited to the structure of the seventh gas sensor 110. For example, an eighth gas sensor 111 shown in FIG. 13 may be adopted, in which the tubular portion 10a of the metal shell protecting member 10 is formed long, and the rear end of the tubular portion 10a is in contact with at least one of the ceramic holder 61 and the metal holder 71 over the entire circumference. That is, in the eighth gas sensor 111, the metal shell protecting member 10 covers a region, of the inner surface of the through-hole 57, on the front side relative to the ceramic holder 61, and is in contact with at least one of the ceramic holder 61 and the metal holder 71.

When the eighth gas sensor 111 is provided with the metal shell protecting member 10 of the above structure, the inner surface of the through-hole 57 is prevented from being in direct contact with the exhaust gas, whereby corrosion of the third metal shell 117 due to the exhaust gas can be suppressed. Thus, falling of a part of the third metal shell 117 due to corrosion is suppressed, and attachment of chips of the third metal shell 117, which have fallen off due to corrosion, to the detection element 5 is suppressed, thereby suppressing occurrence of an error in a sensor output due to the chips. Also in the eighth gas sensor 111, the same effects as those of the first embodiment can be achieved by providing the metal shell protecting member 10, whereby the heat resistance can be improved while including the third metal shell 117 formed of a material that can be subjected to working accompanied with deformation.

In the above embodiments, the metal shell protecting member is formed of a single member. However, the metal shell protecting member may be composed of a plurality of members. Further, a plurality of metal shell protecting members may be stacked.

The type of the sensor of the present invention is not limited to the gas sensor that detects gas concentration as the state quantity of a measurement target. A temperature sensor that detects the temperature of a measurement target is also within the scope of the present invention.

DESCRIPTION OF REFERENCE NUMERALS 1 gas sensor
3 metal shell
3a protector fixing portion
3b protector opposing surface
5 detection element
9 element protector
9a outer protector
9b inner protector
9c hole
10 metal shell protecting member
10a tubular portion
10b flange portion
10c insertion hole
55 screw portion (external thread portion)
57 through-hole
61 holder (ceramic holder)
81 second metal shell protecting member
81a rear-side tubular portion
81b step portion
81c front-side tubular portion
81d inward projecting portion
81e insertion hole
83 third metal shell protecting member
83a rear-side tubular portion
83b step portion
83c front-side tubular portion
83d insertion hole
85 fourth metal shell protecting member
85a inner-side tubular portion
85b connecting portion
85c outer-side tubular portion
85d insertion hole
101 second gas sensor
103 third gas sensor
105 fourth gas sensor
107 fifth gas sensor
109 sixth gas sensor
110 seventh gas sensor
111 eighth gas sensor
113 second metal shell
113a protector fixing portion
113b protector opposing surface
113c flange portion
115 attachment member
117 third metal shell
117a protector fixing portion
117b protector opposing surface
117c crimping fixing portion
119 second element protector
119a second outer protector
119b second inner protector
119c hole
119d outer bent portion
119e inner bent portion
120 welded portion
A1 protector internal region

The invention claimed is:
1. A sensor comprising:
a sensor element that is formed in an elongated shape extending in an axial direction, and includes a detection portion at a front side thereof;
a metal shell that is formed in a tubular shape having a through-hole extending from a front-side opening thereof to a rear-side opening thereof, and holds the sensor element via an element holding member, the sensor element being disposed in the through-hole, with the detection portion projecting from the front-side opening;

a tubular element protector that includes an opening, through which a measurement target passes, and is fixed to a front side of the metal shell, and a metal shell protecting member, wherein the metal shell includes, at an outer surface thereof, a protector opposing surface that opposes a rear end portion of the element protector, the metal shell protecting member is configured to cover, together with the element protector, at least a part of a front end surface of the metal shell, at least a part of an inner surface of the through-hole, and at least a part of a radial outer surface of the metal shell, which is connected with the front end surface of the metal shell, and wherein the metal shell protecting member is formed of a material having corrosion resistance higher than that of the metal shell.

2. The sensor according to claim 1, wherein when a protector internal region is defined to include: a region of an inner surface of the through-hole of the metal shell, which is provided on the front side relative to the element holding member; a region of the radial outer surface of the metal shell, which is covered with the element protector; and the front end surface of the metal shell, the metal shell protecting member and the element protector cover at least a region of the protector internal region of the metal shell, which is provided on the front side relative to the protector opposing surface.

3. The sensor according to claim 1, wherein the metal shell protecting member is formed in a tubular shape having an insertion hole through which the sensor element is inserted.

4. The sensor according to claim 1, wherein the metal shell protecting member includes a protector contact portion that is in contact with an inner surface of the element protector over a circumferential direction.

5. The sensor according to claim 1, wherein an inward projecting portion that projects inward is provided at a rear side of the metal shell protecting member.

6. The sensor according to claim 1, wherein the metal shell protecting member is formed of a metal material.

7. The sensor according to claim 1, wherein the metal shell protecting member covers a region, of the inner surface of the through-hole, on the front side relative to the element holding member, and is in contact with the element holding member.

8. The sensor according to claim 7, wherein the element holding member includes: a ceramic holder that is in contact with the sensor element; and a metal holder that is disposed outward relative to the ceramic holder and is in contact with the metal shell, and the metal shell protecting member covers a region of the inner surface of the through-hole, which is provided on the front side relative to the element holding member, and is in contact with at least one of the ceramic holder and the metal holder.

9. A sensor comprising:

a sensor element that is formed in an elongated shape extending in an axial direction, and includes a detection portion at a front side thereof;

a metal shell that is formed in a tubular shape having a through-hole extending from a front-side opening thereof to a rear-side opening thereof, and holds the sensor element via an element holding member, the sensor element being disposed in the through-hole, with the detection portion projecting from the front-side opening;

a tubular element protector that includes an opening, through which a measurement target passes, and is fixed to a front side of the metal shell, and a metal shell protecting member, wherein the metal shell includes, at an outer surface thereof, a protector opposing surface that opposes a rear end portion of the element protector, and the metal shell protecting member is configured to cover, together with the element protector, at least a part of a front end surface of the metal shell, at least a part of an inner surface of the through-hole, and at least a part of a radial outer surface of the metal shell, which is connected with the front end surface of the metal shell, and the metal shell protecting member is formed of a material superior in heat resistance to the metal shell.

10. A sensor comprising:

a sensor element that is formed in an elongated shape extending in an axial direction, and includes a detection portion at a front side thereof;

a metal shell that is formed in a tubular shape having a through-hole extending from a front-side opening thereof to a rear-side opening thereof, and holds the sensor element via an element holding member, the sensor element being disposed in the through-hole, with the detection portion projecting from the front-side opening;

a tubular element protector that includes an opening, through which a measurement target passes, and is fixed to a front side of the metal shell, and a metal shell protecting member, wherein the metal shell includes, at an outer surface thereof, a protector opposing surface that opposes a rear end portion of the element protector, the metal shell protecting member is configured to cover, together with the element protector, at least a part of a front end surface of the metal shell, at least a part of an inner surface of the through-hole, and at least a part of a radial outer surface of the metal shell, which is connected with the front end surface of the metal shell, and the detection portion protrudes through a front end of the metal shell protecting member in the axial direction.

11. The sensor according to claim 10, wherein the radial outer surface of the metal shell is covered by the element protector.

* * * * *